United States Patent [19]

Lee et al.

[11] Patent Number: 5,200,537

[45] Date of Patent: Apr. 6, 1993

[54] PROCESS FOR PREPARING METALLOCENES

[75] Inventors: John Y. Lee; Steven P. Diefenbach, both of Baton Rouge, La.

[73] Assignee: Ethyl Corporation, Richmond, Va.

[21] Appl. No.: 923,646

[22] Filed: Aug. 3, 1992

[51] Int. Cl.$^5$ .......................... C07F 7/28; C07F 11/00
[52] U.S. Cl. ........................ 556/11; 556/12; 556/53
[58] Field of Search .............. 556/11, 12, 53

[56] References Cited

U.S. PATENT DOCUMENTS 3,224,935 12/1965 Burt ........................ 167/30
5,071,808 12/1991 Antberg et al. ................ 502/107
5,117,020 5/1992 Razavi ........................ 556/43

OTHER PUBLICATIONS

R. A. Newmark, et al., Inorg. Chem. Feb. 20, 1991, 30, pp. 853–856, "NMR Assignments of Alkylcyclopentadienyl Ligands in Zirconium and Platinum Complexes".
J. C. S. Dalton, Feb. 7, 1981, pp. 805–813, "Metallocene Derivatives of Early Transition Metals. Part 2.$^1$ Substituted Cyclopentadienyl Group 4A Dichloro–metallocene Complexes [M ($\eta$-C$_2$H$_4$R)$_2$Cl$_2$] (M=Zr or Hf; R=Me, Et, Pr$^i$, Bu$^t$, or SiMe$_3$), their Mono- and Di-alkyl Derivatives [M ($\eta$-C$_5$H$_4$R)$_2$R'X] (X=Cl or R'; R'=CH$_2$SiMe$_3$ or CH$_2$CMe$_3$), and their d$^1$ Reduction Products", by Michael F. Lappert, et al.
J. Am. Chem. Soc. Sep. 25, 1991, 113, pp. 7594–7602, "Cp-Substituent Additivity Effects Controlling the Stereochemistry of the Propene Polymerization Reaction at Conformationally Unrestricted (Cp–CHR$^1$R$^2$)$_2$ZrCl$_2$/Methylalumoxane Catalysts", Gerherd Erker, et al.
Wilkinson et al., J. Am. Chem. Soc., vol. 76, No. 17, pp. 4281–4284, (1954).
Sullivan et al., J. Orgamomet. Chem., vol. 8, pp. 277–285 (1967).
Reynolds et al., J. Inorg. Nucl. Chem., vol. 9, pp. 86–92 (1959).

*Primary Examiner*—Jose G. Dees
*Assistant Examiner*—Porfirio Nazario
*Attorney, Agent, or Firm*—David M. Bunnell

[57] ABSTRACT

A process is provided for preparing a transition metal compound of the formula: (RC$_5$H$_4$)$_2$MX$_2$, where R is hydrocarbyl or silahydrocarbyl of 1 to 10 carbon atoms, M is titanium or zirconium and X is halogen. The process comprises the steps of:

(a) reacting Na(C$_5$H$_5$) with RX, where R and X are as defined above, in an organic solvent so as to form a reaction product mixture which includes RC$_5$H$_4$ and C$_5$H$_5$;

(b) vacuum stripping the product mixture at ambient temperatures so as to remove substantially all of said C$_5$H$_5$ from said product mixture;

(c) deprotonating the RC$_5$H$_4$; and (d) adding MX$_4$, where M and X are as defined above, to the product mixture so as to react the RC$_5$H$_4$ and the MX$_4$ and form said transition metal compound, the transition metal compound being substantially free of C$_5$H$_5$ containing impurities.

12 Claims, No Drawings

PROCESS FOR PREPARING METALLOCENES

This invention relates generally to the preparation of metallocene derivatives which are useful as olefin polymerization catalysts and more specifically to an improved process for preparing bis(monosubstituted cyclopentadienyl) transition metal metallocenes which are substantially free of unsubstituted cyclopentadienyl impurities.

Metallocene derivatives represented by the formula $(RCp)_2MX_2$, where R is hydrocarbyl or silahydrocarbyl of 1 to 20 carbon atoms, Cp is cyclopentadienyl $(C_5H_4—)$, M is titanium or zirconium and X is halogen are known to be useful catalysts for olefin polymerization. They can be prepared by reacting a deprotonated RCp compound with $MX_4$. As noted in the literature, however, the generation of RCp by the alkylation of cyclopentadiene using alkyl halides is difficult due to the generation of a complex mixture of products (Inorg. Chem. 1991, 30, 856-858). This reference proposes the use of either a liquid ammonia (low temperature) reaction medium or a highly reactive alkylating agent, such as ethyl trifluoromethanesulfonate. Furthermore, the use of alkylhalides always results in a product which contains, due to the reaction equilibrium, cyclopentadiene and cyclopentadiene dimer. The dimer is inert in the subsequent metallocene preparation, but the cyclopentadiene must be removed. Otherwise, it will form $(Cp)_2MX_2$ impurities which adversely change the molecular weight distributions of the polymers produced when the $(RCp)_2MX_2$ metallocene product is used to catalyze olefin polymerization. Heretofore, complete removal of cyclopentadiene has not been achieved because of the generation of additional cyclopentadiene due to the cracking of the cyclopentadiene dimer. We have now discovered an economical, one-pot process for making such transition metal metallocenes which are free of Cp impurities. Furthermore, the process can be conducted at ambient temperatures which avoids the cost of refrigeration cooling systems.

In accordance with this invention there is provided a process for preparing a transition metal compound of the formula: $(RC_5H_4)_2MX_2$, where R is hydrocarbyl or silahydrocarbyl of 1 to 20 carbon atoms, M is titanium or zirconium and X is halogen, said process comprising the steps of:
(a) reacting $Na(C_5H_5)$ with RX, where R and X are as defined above, in an organic solvent so as to form a reaction product mixture which includes $RC_5H_4$ and $C_5H_5$;
(b) vacuum stripping said product mixture at ambient temperatures so as to remove substantially all of said $C_5H_5$ from said product mixture;
(c) deprotonating said $RC_5H_4$; and
(d) adding $MX_4$, where M and X are as defined above, to said product mixture so as to react said deprotonated $RC_5H_4$ and said $MX_4$ and form said transition metal compound, said compound being substantially free of $C_5H_5$ containing impurities.

According to the alkylation process, NaCp is reacted with an alkyl halide in a solvent. The NaCp is commercially available and can be prepared by cracking cyclopentadiene dimer and reacting the cyclopentadiene with sodium metal as is known in the art. The preferred alkyl halides are represented by the formula RX, where R is $C_1$ to $C_{20}$ (and more preferably $C_4$ to $C_{10}$) hydrocarbyl or silahydrocarbyl such as, for example, methyl, ethyl, n-propyl, isopropyl, n-butyl, tert-butyl, isobutyl, pentyl, hexyl, heptyl, trimethylsilyl, and the like and X is 10 halogen. Bromine is the preferred halogen. Chlorine can be used but gives slower reaction rates and iodine is more expensive. The NaCp and RX reactants are preferably used in NaCp:RX mole ratios of about 1:1, in order to minimize the substituted or unsubstituted Cp and $Cp_2$ amount of dialkyl substituted or unsubstituted Cp and $Cp_2$ (cyclopentadiene dimer) by-products, but ratios of about 1:0.8 to 1:1.2 can be used. The preferred solvents for the reaction are ethers (e.g. THF, diethylether and the like) but hydrocarbon solvents can also be used such as benzene, toluene, and the like. Preferably, combined reactant concentrations of from about 5 to 20 wt. percent in the solvent, are used. The reaction can be conducted at ambient temperatures with the reaction being exothermic. Generally, the reaction temperature will range from about 20° C. to 50° C. The by-products of the alkylation reaction typically include besides NaCl, minor portions of $R_2Cp$ and $Cp/(Cp_2)$. Surprisingly, we have found that the Cp can be substantially completely removed (less than about 1 wt. percent) by reducing the volume of the reaction mixture under vacuum (2-15 mm Hg) at temperatures of about 0° C. to 25° C. The cyclopentadiene dimer remains, but is inert so long as the subsequent reactions and product work-up procedures avoid elevated temperatures which would cause cracking to form additional cyclopentadiene. The metallocene by-products resulting from the presence of some disubstituted cyclopentadiene $(R_2Cp)$ can be easily separated from the final metallocene product by solvent separation. The vacuum treatment also removes any unreacted alkyl halide which can then be recycled. Reduction of the volume of the reaction mixture to about 25% is sufficient to remove substantially all of the cyclopentadiene (no Cp was detected by GC such that the Cp content was less than about 0.1%.)

The product RCp can then be deprotonated in situ with, for example, Na powder, BuLi, NaH, LiH or a Grignard reagent (RMgX). Solvent can be added back to the reaction mixture prior to deprotonation. Preferably, about a 1:1 mole ratio of RCp to deprotonating agent is used. No more than a 10% excess of deprotonating agent is necessary or desirable as we have found that salt formation with the mono-alkyl product is favored over the dialkyl $(R_2Cp)$ impurity. The deprotonation can be carried out at ambient temperatures and cooling is unnecessary, although higher or lower temperatures of about $-30°$ C. to 60° C. can also be used. If sodium is used as the deprotonating agent, then excess sodium metal must be filtered from the reaction mixture prior to the further reaction with the transition metal halide to form the product bis(mono-alkylcyclopentadienyl) transition metal metallocene.

The $(RCp)_2MX_2$ metallocene derivatives are prepared by adding a transition metal halide of titanium or zirconium, e.g. $TiCl_4$ or $ZrCl_4$, to the deprotonated mono-alkylsubstituted cyclopentadiene ligand, preferably in nearly stoichiometric proportions of ligand to transition metal halide (mole ratios of about 1:0.4 to 0.5 ligand to transition metal halide and, more preferably, 1.0:0.5) so as to minimize the formation of $RCpMX_3$ impurities and the amount of unreacted transition metal halide which may be difficult to remove from the product. The process 10 can be carried out at ambient temperature. Generally, the reaction temperatures range from about 20° C. to 40° C.

When using sodium as the deprotonating agent, it is preferable to add the transition metal halide as a solvent solution in an ether solvent such as glyme, diethylether, tetrahydrofuran (THF), and the like. The sodium halide which is formed will precipitate and can be filtered from the product solution. When BuLi is used as the deprotonating agent, LiCl is soluble in tetrahydrofuran but not in diethylether so that the preferred reaction solvent is diethylether. As an alternative when using BuLi, the alkyl cyclopentadiene reactant can be dissolved in diethylether and the BuLi in hexane so as to form a slurry of LiRCp. The transition metal halide such as $ZrCl_4$ powder or $TiCl_4$ can then be added. LiCl will precipitate and can be removed by filtration. Upon stripping the ether, the product (monoalkylCp)$_2$ZrCl$_2$ product will crystallize from the hexane. An advantage of the process of the invention is that it can be carried out as a one-pot process without the need to recover any intermediates. The products can be recrystallized by dissolving them in warm hexane (50° C.) and then cooling the hexane solution to precipitate the purified products.

The process is further illustrated by, but is not intended to be limited to, the following examples.

EXAMPLE 1

BuBr (12 mmol, 1.644 g) and THF (6.0 g, 6.8 ml) were charged to a 50 ml r.b. flask in a dry box. A mixture of NaCp (10 mmol, 0.88 g) and THF (14 ml) was added slowly at 22° C. to 40° C. into above BuBr/THF solution over a period of 15 minutes. The reaction mixture was stirred at 22° C. for 3 hrs. to form a mixture of BuCp (58 mol %), Bu$_2$Cp (21 mol %), Cp/(Cp)$_2$ (21 mol %) based on NaCp charged, and a trace of BuBr. The volume of the above mixture was reduced under vacuum (0° C. to 22° C./2 mm Hg) to 25% of its original volume. GC showed that all the cyclopentadiene and BuBr had been removed and there was 40 mol % of BuCp based on NaCp charged in the product mixture. About 20 ml of THF were then added. Deprotonation with a 10% excess amount of Na powder was performed. The Na was slowly added into above solution at 22° C. over a period of ½ hr. Hydrogen formation was observed. The mixture was then stirred at 22° C. for an additional 2 hrs. $^1$HNMR of the product showed a >95% yield of NaBuCP. After the Na and NaBr were filtered out, the in 4 g. of glyme) at 22° C. which was slowly added into the THF solution of NaBuCp in 5 minutes to form a >90% yield (by $^1$HNMR) of (BuCp)$_2$ZrCl$_2$ which contained no cyclopentadienyl zirconocenes. The glyme and THF were removed and an equal volume of Et$_2$O was added in order to precipitate LiCl, which was then filtered out. Hexane (15 ml) was added, and the Et$_2$O was slowly stripped off at 40° C. to 45° C. The hexane solution was cooled to 22° C. and (BuCp)$_2$ZrCl$_2$ crystallized. The product was filtered out, dried, and weighed. The yield was 56% based on the BuCp used. The $^1$HNMR showed that this product contained 6% (Bu$_2$Cp)$_2$ZrCl$_2$ but no cyclopentadienyl zirconocenes. MP 89°–92° C. (lit 93° C.). Pure product can be obtained by further recrystallization.

EXAMPLE 2

BuCp (94% pure, 6.5 g, 0.05 mole) which was not prepared by the process of Example 1, but was purified by distillation and still contained 6% cyclopentadiene, and 200 ml 2of Et$_2$O were charged to a 500 ml flask in a dry-box. BuLi (0.05 mole, 3.2 g) in 20 ml of hexanes was added slowly with stirring into the above solution (temperature 22° C. to 33° C. over a period of 30 minutes to form a very thick LiBuCp/Et$_2$O slurry. The reaction mixture was stirred at 22° C. for an additional 30 minutes. $^1$HNMR showed a 95% conversion. ZrCl$^4$ powder (0.025 mol) was directly added to the above slurry with stirring (temperature 20° C. to 33° C. over a period of 30 minutes. The reaction mixture was stirred at 22° C. for an additional 30 minutes. $^1$HNMR showed a 95% formation of (BuCp)$_2$ZrCl$_2$. In the Et$_2$O/hexane solvent reaction medium, the LiCl was 100% precipitated. The LiCl was filtered out, 40 ml of hexane were added to the reaction mixture, and the Et$_2$O was stripped off at 40°–45° C. The hexane solution was cooled to 22° C. and (BuCp)$_2$ZrCl$_2$ crystallized. The product (BuCp)$_2$ZrCl$_2$ was filtered out, dried, and weighed. The yield was 74%. An additional 9% (BuCp)$_2$ZrCl$_2$ was recovered from the mother liquor. The product also contained 5% cyclopentadienyl zirconocenes. The example illustrates that the Cp impurity present in the starting BuCp will be carried through into the product metallocene. The example also illustrates an alternate method of deprotonation and product formation which can be used in the process of the invention.

What is claimed is:

1. A process for preparing a transition metal compound of the formula: $(RC_5H_4)_2MX_2$, where R is hydrocarbyl or silahydrocarbyl of 1 to 20 carbon atoms, M is titanium or zirconium and X is halogen, said process comprising the steps of:
   (a) reacting Na($C_5H_5$) with RX, where R and X are as defined above, in an organic solvent so as to form a reaction product mixture which includes $RC_5H_4$ and $C_5H_5$;
   (b) vacuum stripping said product mixture at ambient temperatures so as to remove substantially all of said $C_5H_5$ from said product mixture;
   (c) deprotonating said $RC_5H_4$ and
   (d) adding $MX_4$, where M and X are as defined above, to said product mixture so as to react said deprotonated $RC_5H_4$ and said $MX_4$ and form said transition metal compound, said compound being substantially free of $C_5H_5$ containing impurities.

2. The process of claim 1 wherein said $RC_5H_4$ is deprotonated without recovering said $RC_5H_4$ from the reaction mixture.

3. The process of claim 1 wherein R is $C_4$ to $C_{10}$ hydrocarbyl.

4. The process of claim 1 wherein X is chlorine.

5. The process of claim 1 wherein the compound is bis(n-butylcyclopentadienyl) zirconium dichloride.

6. The process of claim 1 wherein the mole ratio of Na($C_5H_5$) to RX is from about 1:0.8 to 1:1.2 and the mole ratio of deprotonated $RC_5H_4$ to $MX_4$ is from about 1:0.4 to 1:0.6.

7. The process of claim 6 wherein said product mixture is vacuum stripped at a pressure of from about 2–15 mm Hg and temperatures of about 0° to 25° C.

8. The process of claim 7 wherein said organic solvent is selected from the group consisting of ethers, hydrocarbons and any combination thereof.

9. The process of claim 8 wherein said solvent is tetrahydrofuran, RX is n-butylbromide, $MX_4$ is $ZrCl_4$ and the transition metal compound is bis-(n-butylcyclopentadienyl) zirconium dichloride.

10. The process of claim 9 wherein said $RC_5H_4$ is deprotonated with a deprotonating agent selected from the group consisting of Na, NaH, LiH, BuLi and a Grignard reagent.

11. The process of claim 10 wherein said deprotonating agent is Na and said $ZrCl_4$ is added as a solution in an ether solvent.

12. The process of claim 10 wherein said deprotonating agent is BuLi in hexane, said organic solvent is diethylether such that said BuLi and said $R(C_5H_4)$ form a slurry containing $LiBuC_5H_4$ and said $ZrCl_4$ is added as a solid powder to said slurry to form said bis-(n-butylcyclopentadienyl) zirconium chloride and LiCl, which LiCl precipitates and is removed from the product solution.

* * * * *